(12) United States Patent
Hildreth et al.

(10) Patent No.: US 7,393,988 B2
(45) Date of Patent: Jul. 1, 2008

(54) PROCESS FOR PRODUCTION OF ETHYLBENZENE FROM DILUTE ETHYLENE STREAMS

(75) Inventors: James M. Hildreth, Wyckoff, NJ (US); Kerman Nariman Dukandar, Edison, NJ (US); Ronald M. Venner, Franklin Lanes, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 11/825,422

(22) Filed: Jul. 6, 2007

(65) Prior Publication Data
US 2007/0255080 A1   Nov. 1, 2007

Related U.S. Application Data

(62) Division of application No. 10/660,065, filed on Sep. 8, 2003, now Pat. No. 7,259,282.

(51) Int. Cl.
*C07C 2/64* (2006.01)

(52) U.S. Cl. .......................... 585/447; 585/446; 585/448
(58) Field of Classification Search ................. 585/447, 585/446, 448
See application file for complete search history.

(56) References Cited

U.S. PATENT DOCUMENTS 6,177,600 B1 * 1/2001 Netzer ........................ 585/323

* cited by examiner

*Primary Examiner*—Thuan Dinh Dang
(74) *Attorney, Agent, or Firm*—Dilworth & Barrese, LLP

(57) ABSTRACT

An improvement in a process for the production of ethylbenzene from a dilute ethylene stream wherein an ethylene-containing stream derived from a cracking process is directed to an ethylene fractionator for separation of ethylene and ethane. The improvement includes providing the dilute ethylene stream by liquefying and separating out a portion of the ethylene-containing stream prior to directing the remainder of the ethylene-containing stream to the ethylene fractionator and/or by drawing off a side stream from the ethylene fractionator; and, directing the dilute ethylene stream as a feed to an alkylator for alkylation with benzene to produce ethylbenzene.

5 Claims, 5 Drawing Sheets

PROCESS FOR PRODUCTION OF ETHYLBENZENE FROM DILUTE ETHYLENE STREAMS

CROSS REFERENCE TO RELATED APPLICATIONS

This application is a divisional of U.S. application Ser. No. 10/660,065 filed Sep. 8, 2003, now U.S. Pat. No. 7,259,282, incorporated by reference herein, and claims priority thereto.

BACKGROUND OF THE INVENTION

1. Field of the Invention

The invention relates to processes related to the production of ethylbenzene from dilute sources of ethylene.

2. Description of the Related Art

Ethylene is a commonly used unsaturated organic compound which may be used in various processes for the synthesis of more complex compounds. For example, ethylene can be reacted with aromatics to produce alkylaromatics, such as ethylbenzene, and with butenes to produce propylene. Ethylbenzene is commonly used to produce styrene, which may be polymerized to produce polystyrene. Propylene is commonly used for the manufacture of polypropylene.

The process for producing high purity ethylene is well known, and involves pyrolysis of a hydrocarbon feed and subsequent separation of ethylene and reaction by-products by distillation. The process generally comprises the following: A feedstock comprising ethane, propane, butane, naphtha, gas oils or hydrocracked vacuum gas oils is fed to an ethylene plant, where it is thermally cracked in the presence of steam in a bank of pyrolysis furnaces. An olefin-bearing effluent gas is formed and is quenched progressively by generating steam and through direct contact with oil and/or water. The effluent is compressed in a multi-stage centrifugal compressor, acid gases are removed by amine treating and/or a caustic wash, and then the gases are dried over a molecular sieve. Methane offgas is recovered under cryogenic conditions in a demethanizer. Ethylene and ethane are then recovered together in a deethanizer. Acetylene is normally catalytically removed and then an ethylene product recovery takes place under low temperature conditions in a final fractionation column. Just prior to final fractionation the ethylene stream will include significant amounts of ethane (15% to 35%) and relatively small amounts of hydrogen, methane and propylene. Final fractionation results in a high purity (polymer-grade) ethylene (at least about 99.95 mole %,) and recycle ethane, which may be used to produce more ethylene. Variations of this scheme also exist including schemes where the deethanization, depropanization and/or acetylene removal steps may precede the demethanization step. In all cases a final fractionation of ethylene-ethane is employed to produce high purity ethylene product.

The final fractionation of the ethylene mixture is relatively energy intensive and it would be preferable to reduce the amount of ethylene/ethane processed in this manner, or to eliminate this step altogether. However, many processes, including those to produce propylene and ethylbenzene, typically are carried out with a feed of high purity ethylene. Ethylene streams diverted from the ethylene plant, after acetylene removal but before final fractionation, typically contain only about 65 mol %, ethylene when ethane crackers are the source of the ethylene, and about 85 mol % ethylene when naphtha crackers are the source of the ethylene; the primary difference between the two processes being the feedstock used and a somewhat simpler recovery section for the ethane cracker (i.e., the ethane cracker has fewer distillation columns since heavy byproduct formation is reduced).

A number of processes for producing alkylaromatics, such as ethylbenzene, are also known, and may employ fixed-bed or catalytic distillation type processes. The fixed-bed process generally comprises the following: Benzene is sent to an alkylator containing a fixed bed of alkylation catalyst and reacted with ethylene to yield a mixture of alkylated benzenes and excess benzene. The mixture is fractionated to recover ethylbenzene, recycle benzene, and higher ethylated benzenes. The recycle benzene is sent back to the alkylator to react with additional ethylene and to a transalkylator, where the higher ethylated benzenes are transalkylated with the benzene to form additional ethylbenzene.

While polymer-grade ethylene is preferable for these processes, ethylbenzene can also be produced from relatively dilute ethylene feeds. In this event, catalytic distillation reactors are preferred because ethylene feeds as dilute as about 15 mol % can be utilized to produce ethylbenzene. If the fixed-bed process is used with dilute ethylene feeds, ethylene with a purity as low as about 60 mol % can be used, provided the remaining 40 mol % of the feed contains minimal hydrogen and methane content. Dilute ethylene from an ethane cracker may have relatively low amounts of methane and hydrogen, but this may not always be the case since, for example, dilute ethylene from an ethylene plant with a front-end deethanizer may contain larger quantities of hydrogen and methane. Alternatively, dilute ethylene from a fluid catalytic cracker (FCC) may contain very large quantities of hydrogen or methane if they are not separated at a FCC vapor recovery unit by compression and distillation of FCC off-gas. Typically, the ethane and lighter gases from the FCC do not undergo further separation—rather they are sent to a fuel gas system in the refinery. In any event, fixed-bed processes will incur an energy penalty when the ethylene feed purity is below about 83 mol %.

The energy penalty includes additional energy which must be used in the ethylbenzene plant when ethylene sources used are very dilute. For example, in the ethylbenzene plant described above, additional energy may be needed to recover aromatics from vent gases. Such additional processing may involve refrigerated vent condensers and/or an absorption/stripping system with reboilers and condensers.

The advantages of the invention include significant energy, and consequently cost, savings by eliminating or reducing the final fractionation of ethylene in the ethylene plant.

SUMMARY

An improved process is provided herein for the production of ethylbenzene from a dilute ethylene stream wherein an ethylene-containing stream derived from a cracking process is directed to an ethylene fractionator for separation of ethylene and ethane. The improvement comprises (a) providing the dilute ethylene stream by (i) liquefying and separating out a portion of the ethylene-containing stream prior to directing the remainder of the ethylene-containing stream to the ethylene fractionator and/or by (ii) drawing off a side stream from the ethylene fractionator; and, (b) directing said dilute ethylene stream as a feed to an alkylator for alkylation with benzene to produce ethylbenzene.

The process advantageously saves costs by reducing the amount of energy required for ethylene fractionation.

BRIEF DESCRIPTION OF THE DRAWINGS

Various embodiments are described below with reference to the drawings wherein.

DETAILED DESCRIPTION OF THE PREFERRED EMBODIMENTS

Figure 1:
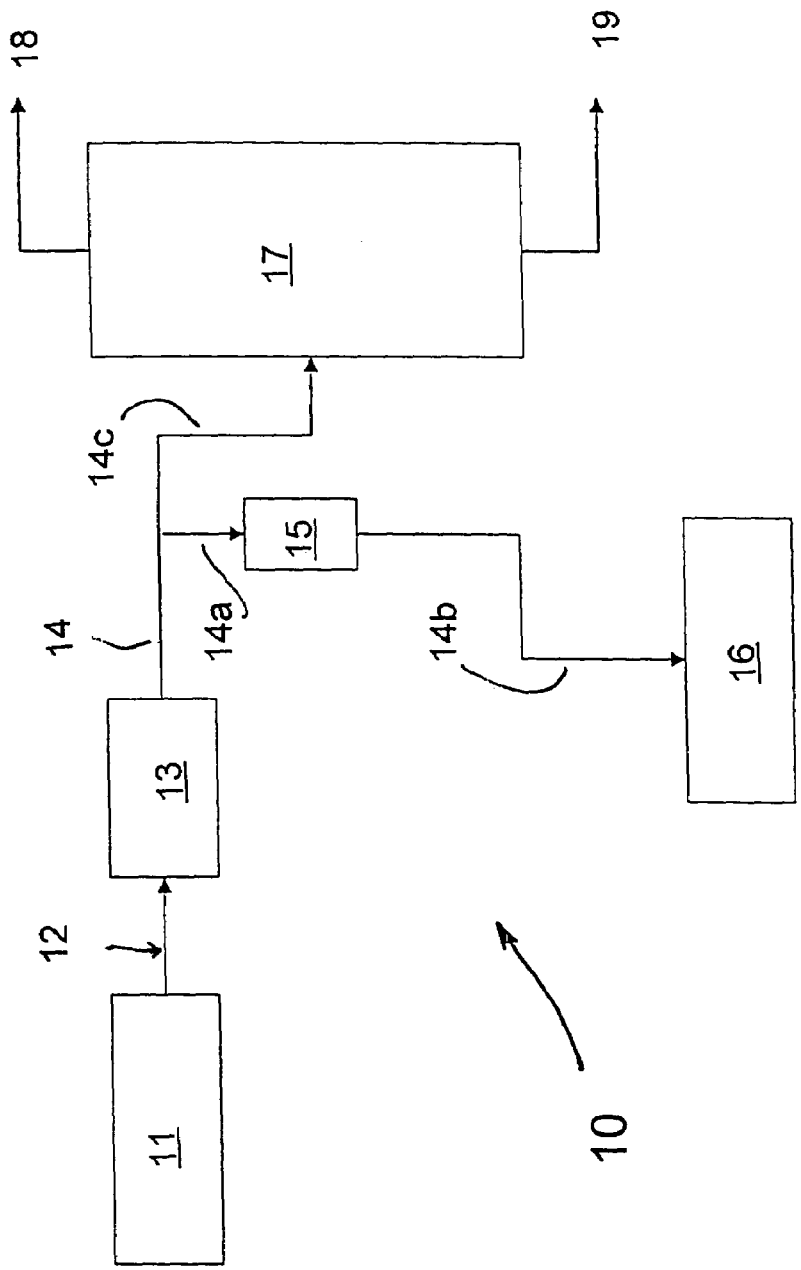
FIG. 1 is a schematic diagram illustrating an ethylbenzene process of the invention wherein a dilute ethylene stream is provided by condensing a portion of an ethylene-containing stream to form a dilute ethylene liquid stream which is sent to an alkylator.

The invention relates to processes for producing dilute ethylene, and using the dilute ethylene to produce ethylbenzene. Dilute ethylene streams from cracking processes typically contain from about 60 mol % to about 85% ethylene with the remainder being mostly ethane with minor amounts of methane and/or hydrogen.

While individual processes for producing ethylene, and ethylbenzene are known, the present invention combines the processes in a manner which is designed to improve overall efficiency and, consequently, reduce the total costs-associated with the production of ethylbenzene.

Generally, preferred processes of the invention comprise diverting a dilute ethylene stream from an ethylene plant at a point subsequent to acetylene removal. The ethylene plant includes the cracking of a hydrocarbon feed such as ethane, propane, butane, naphtha, gas oil, hydrocracked vacuum gas oil and combinations thereof.

In one embodiment the method of the present invention provides dilute ethylene for the production of ethylbenzene wherein a dilute ethylene stream containing ethylene and ethane is withdrawn from the ethylene plant at a point downstream of acetylene removal and upstream of final ethylene product fractionation. The ethylene-content of the dilute ethylene feed is at least about 60 mol %. By withdrawing dilute ethylene from the effluent of the actetylene remover and before the final fractionation step, significant capital and energy saving can be achieved in the ethylene plant because the ethylene/ethane mixture sent to the ethylbenzene plant does not need to be fractionated, thereby saving the fractionation energy. Dilute ethylene can be supplied by subjecting the entire effluent of the acetylene remover to a cooling process in which part of the effluent is condensed to a liquid, or fully condensing only a portion of the effluent. Partial condensing produces a slightly more dilute feed to the ethylbenzene plant and enriches the remaining stream sent as feed to the ethylene fractionator. Fully condensing only a portion of the effluent has the advantage of producing the richest ethylbenzene feed (about 83% for a typical naphtha cracker). Savings are achieved by reducing the ethylene/ethane processed in the ethylene fractionator. In the case of partial condensation, some savings in reflux are also achieved due to feed enrichment. These two cases are detailed below.

In another embodiment the dilute ethylene stream is withdrawn from the ethylene plant as a side draw from the ethylene fractionation column. By withdrawing dilute ethylene as a side-draw from the final fractionation step, significant capital and energy savings can be achieved in the ethylene plant because the ethylene/ethane mixture sent to the ethylbenzene plant does not need to be fully fractionated, thereby saving the fractionation energy. Side-draw can be taken as a liquid or vapor from either the stripping or rectification section. If taken from the rectification section, dilute ethylene of at least 83% purity can be readily produced, thereby eliminating any energy penalty in the ethylbenzene plant. These cases are summarized below.

The dilute ethylene streams are then sent to an alkylator for alkylation with benzene to produce ethyl benzene. Various processes for the production of ethylbenzene from the alkylation of ethylene and benzene are known. Suitable processes for the alkylation of dilute ethylene streams are set forth in commonly assigned copending patent applications Ser. No. 10/372,449 filed Feb. 25, 2003 and Ser. No. 10/376,683 filed Feb. 28, 2003, both of which are incorporated by reference herein in their entirety.

Referring now to FIG. 1, a process 10 for the production of ethylbenzene from a dilute ethylene stream is shown. More particularly, the deethanizer 11 of a conventional ethylene plant provides a $C_2$ vapor stream 12 containing ethylene, ethane and acetylene, which is then sent to an acetylene removal unit 13 for the removal of acetylene preferably by partial hydrogenation in a catalytic reactor to form more ethylene. Optionally, unit 13 can alternatively be an acetylene recovery unit which separates out acetylene rather than converting it. The resulting effluent stream 14, containing at least about 60 mol % ethylene is then divided into a dilute ethylene stream 14a and a remainder 14c of the ethylene-containing steam which is directed to the ethylene fractionator 17 as a feed. The ethylene fractionator 17 separates the ethylene-containing stream 14c into a high purity ethylene fraction 18 (at least about 99.95 mol % pure ethylene) and an ethane fraction 19. The ethane is preferably recycled to the cracking units. The dilute ethylene stream 14a containing at least about 60 mol % ethylene is sent to a condenser 15 wherein stream 14a is totally condensed to liquid stream 14b, which is then sent to a conventional ethylbenzene process 16. The amount of dilute ethylene stream 14a drawn off from the acetylene reactor effluent 14 depends upon the ethylene requirements for the ethylbenzene process. In this case the ethylene content of the dilute ethylene stream 14b is the same as the ethylene content of the ethylene fractionator feed 14c. The high purity ethylene stream 18 from the ethylene fractionator 17 can be used for polymerization processes, alkylation processes, or any process where high purity ethylene is required, as well as those in which dilute ethylene can be employed.

Figure 2:
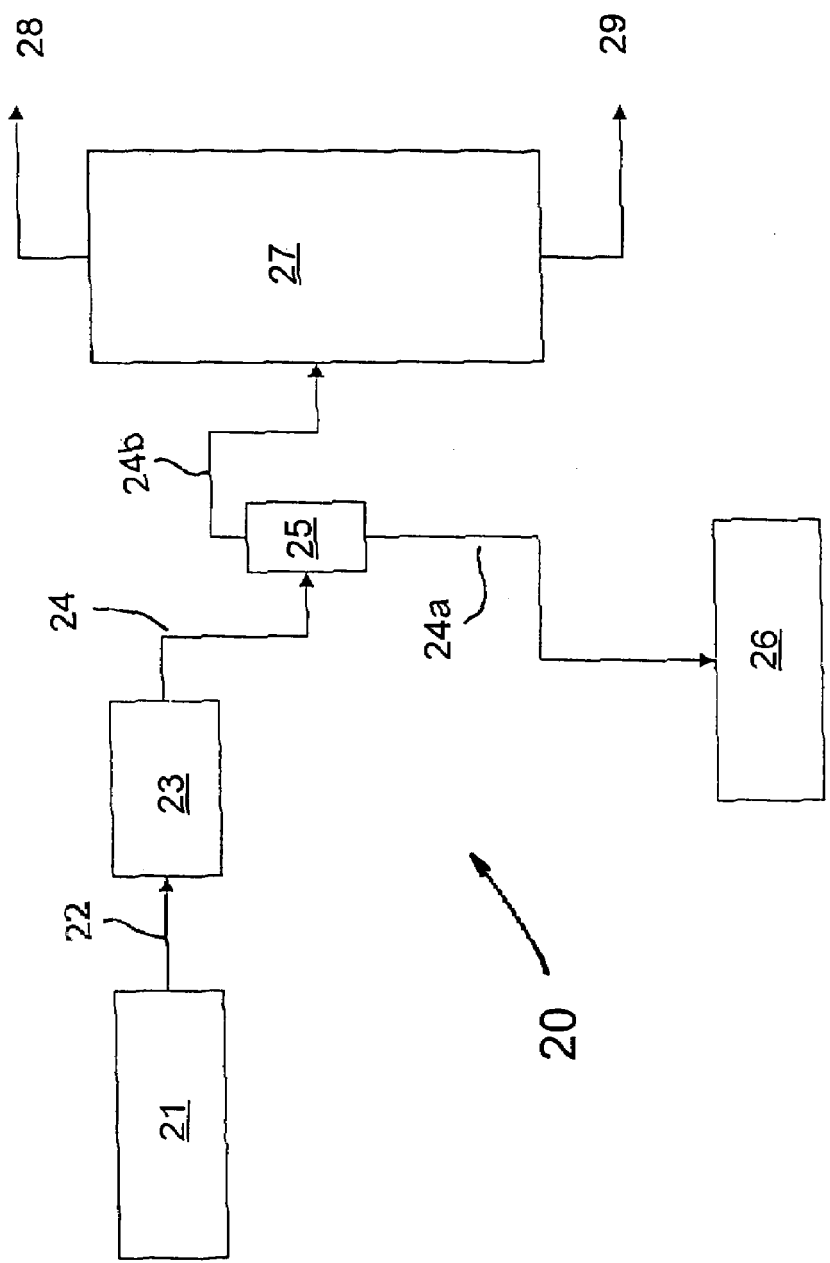
FIG. 2 is a schematic diagram illustrating an ethylbenzene process of the invention wherein an ethylene-containing stream is partially condensed to form a dilute ethylene liquid which is sent to an alkylator.

Referring to FIG. 2 an alternative embodiment 20 of the method of the present invention is illustrated wherein a $C_2$ vapor stream 22 from deethanizer 21 is sent to an acetylene removal unit 23 for the removal of acetylene by partial hydrogenation or acetylene recovery. The entire resulting effluent stream 24 is sent to a cooler 25 wherein a part of the ethylene-containing stream is condensed to a liquid dilute ethylene stream 24a which is then sent to a conventional ethylbenzene process 26. The remaining cooled but uncondensed portion 24b of the ethylene-containing effluent stream is sent as a vapor to ethylene fractionator 27 for separation into an overhead high purity ethylene stream 28 and bottom ethane stream 29. In this case the uncondensed portion 24b of the ethylene-containing stream is richer in ethylene content than the dilute ethylene stream 24a.

Figure 3:
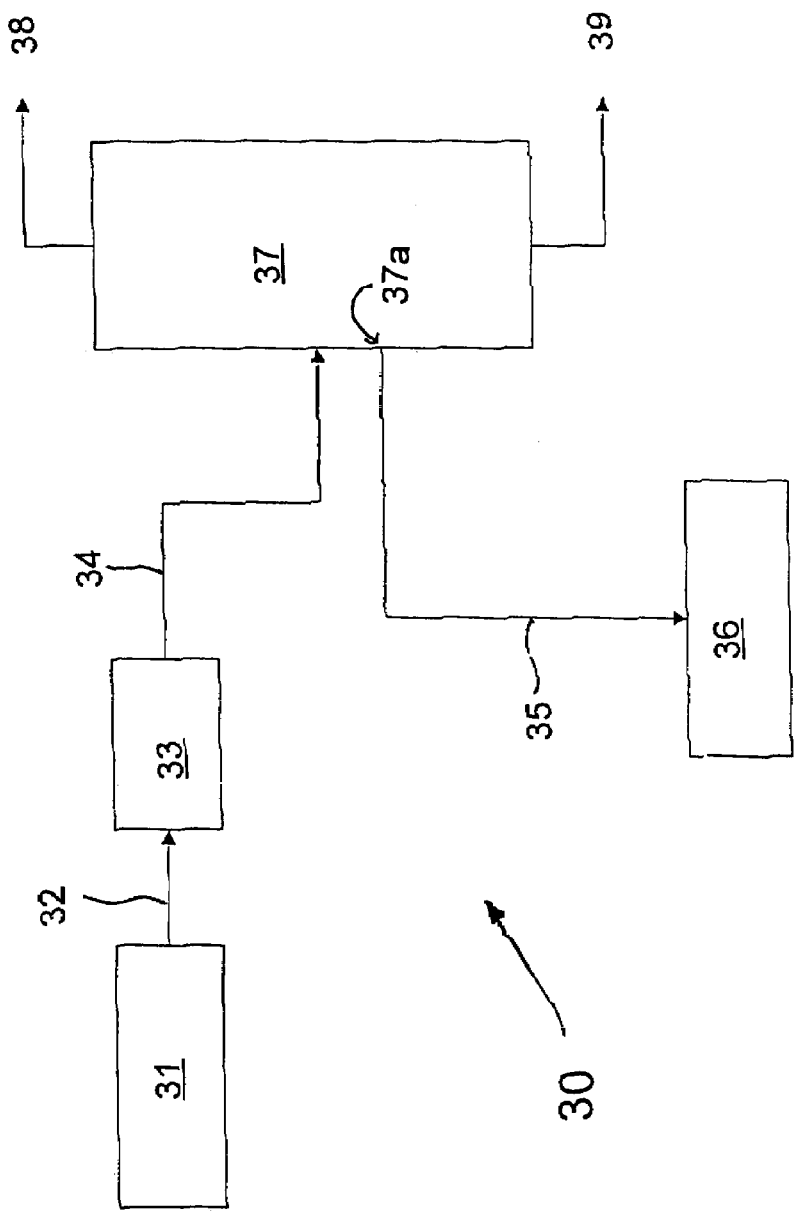
FIG. 3 is a schematic diagram illustrating an ethylbenzene process of the invention wherein a dilute ethylene stream is taken as a side draw from the stripping section of an ethylene fractionator.

Referring now to FIG. 3, yet another embodiment 30 of the present invention is illustrated wherein a $C_2$ vapor stream 32 from a deethanizer 31 is sent to an acetylene removal unit 33 for the removal of acetylene by partial hydrogenation or acetylene recovery. The resulting effluent stream 34 is sent to ethylene fractionator 37 for separation into an overhead high purity ethylene stream 38 and an ethane bottoms 39. A liquid or vapor stream 35 of dilute ethylene is drawn from the side of the stripping portion ethylene fractionator at point 37a, and is then sent to the ethylbenzene process 36. The point 37a at which the dilute ethylene is withdrawn from the ethylene fractionator may be the feed tray or one or two trays below the feed tray such that the ethylene content of the sidedraw is at least about 60 mol %. The actual location will vary depending on the ethylene fractionator feed composition. The amount of liquid or vapor drawn off depends upon the ethylene requirements of the ethylbenzene process.

Figure 4:
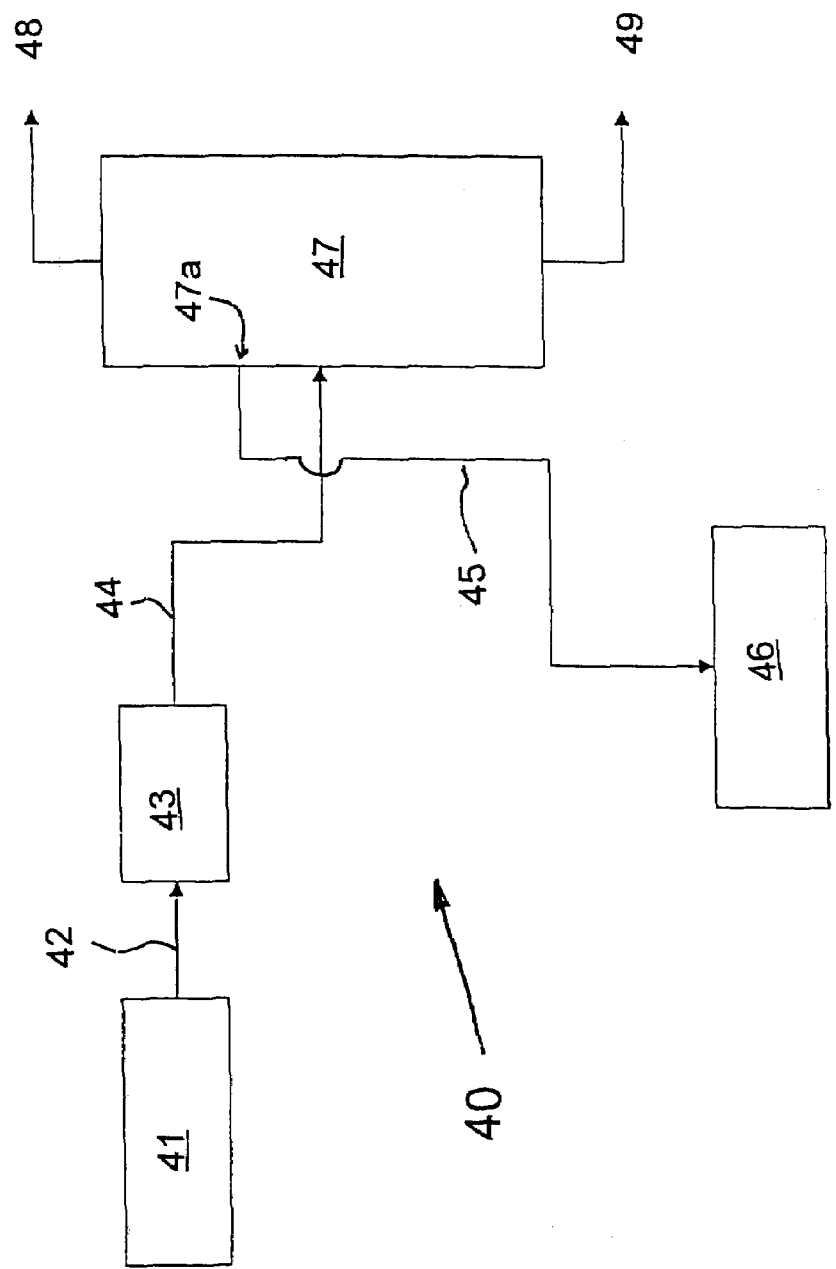
FIG. 4 is a schematic diagram illustrating an ethylbenzene process of the invention wherein a dilute ethylene stream is taken as a side draw from the rectification section of an ethylene fractionator.

Referring to FIG. 4, yet another embodiment 40 of the invention is shown wherein a $C_2$ vapor stream 42 from a deethanizer 41 is sent to an acetylene removal unit 43 for the removal of acetylene by partial hydrogenation or acetylene recovery. The resulting effluent stream 44 is then sent to ethylene fractionator 47 for separation into an overhead high purity ethylene stream 48 and an ethane bottoms 49. A liquid or vapor stream 45 of dilute ethylene is drawn from the side of the ethylene fractionator rectification section at point 47a and is then sent to the ethylbenzene process 46. The point 47a at which the dilute ethylene is withdrawn from the ethylene fractionator may be ten to fifteen trays above the feed tray such that the ethylene content of the sidedraw is at least about 82 mol %. The actual location will vary depending on the ethylene fractionator feed composition. The amount of liquid or vapor drawn off depends upon the ethylene content of the stream 45 and the ethylene requirements of the ethylbenzene process.

Figure 5:
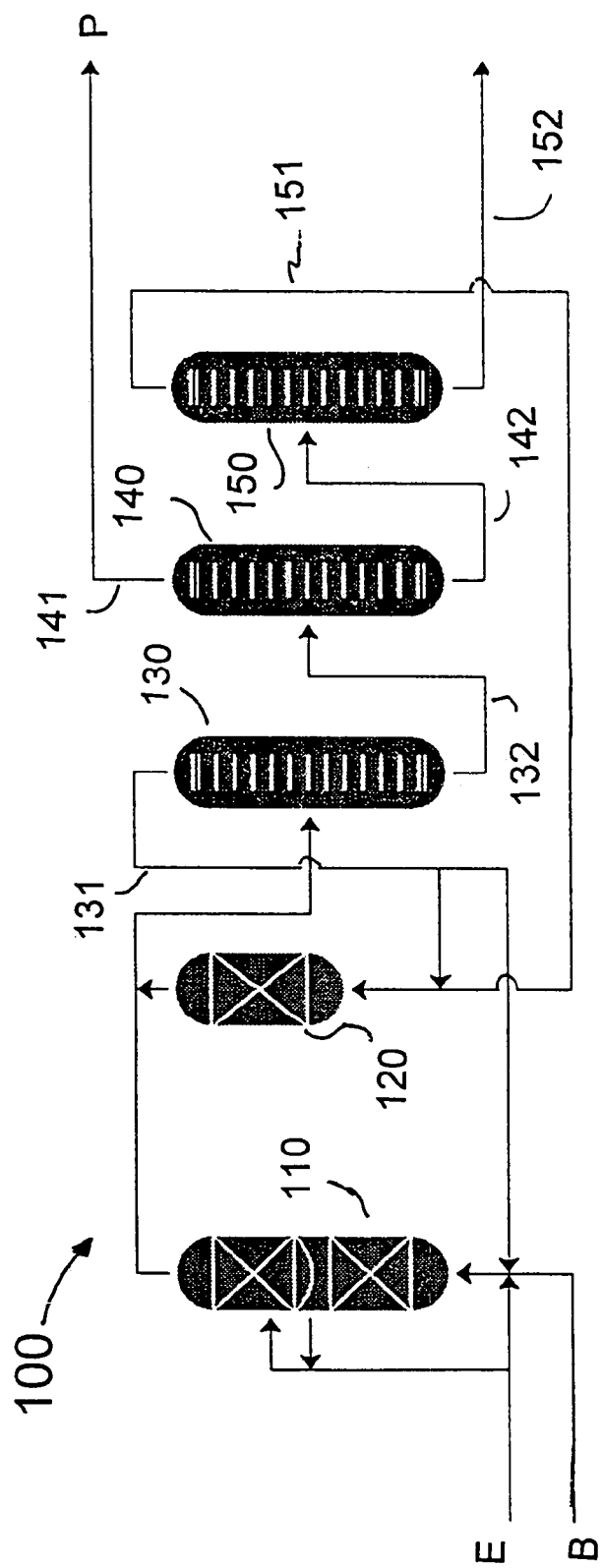
FIG. 5 is a schematic illustration of a process for producing ethylbenzene from ethylene and benzene.

Referring now to FIG. 5 a process for producing ethylbenzene by the alkylation of benzene with ethylene is illustrated in a schematic diagram wherein ethylbenzene process 100 receives a dilute ethylene feed E such as that provided from the process described above (e.g., streams 14b, 24a, 35, and 45 in FIGS. 1 to 4), which is fed into alkylator 110 along with benzene feed B. The overhead from the alkylator 110 is sent to fractionator 130 from which a benzene overhead 131 is recycled back to the alkylator 110 and transalkylator 120. The bottoms 132 from fractionator 130 is sent to fractionator 140. The overhead 141 from fractionator 140 is an ethylbenzene product P. The bottom stream 142 from fractionator 140 are sent to fractionator 150. The overhead 151 from fractionator 150 contains polyethylbenzene which is recycled back to the transalkylator 120 for conversion to ethylbenzene. The bottom stream 152 includes a heavy end fraction. The product ethylbenzene P can be sent to further processing for conversion to styrene monomer. The heavy ends 152 can be used as fuel.

Various aspects of the invention are illustrated by the Examples given below.

EXAMPLE 1

In a system such as that illustrated in FIG. 1, a portion of the effluent 14 is drawn off as dilute ethylene stream 14a which is totally condensed to produce a liquid equivalent to the amount of ethylene required for ethylbenzene production and is sent to ethylbenzene plant 16 as a liquid stream 14b. The remaining stream 14c is sent to the ethylene fractionator 14 as a vapor. This case reduces the feed to the ethylene fractionator 17. Energy is saved in the ethylene fractionator 17 but partly lost in the form of lower recuperation from ethane recycle and in the form of higher reflux requirements in the deethanizer 11 to reduce the propylene content of the deethanizer overhead (dilute ethylene). Propylene content of the dilute ethylene must be sufficiently low to prevent the excessive formation of cumene in the ethylbenzene unit. Cumene, if formed, will be present as an impurity in the ethylbenzene product and is typically limited to 500 ppm or less. The purity of the ethylene feed 14b in this case is about 80 mol % to about 83 mol%. The operating cost savings for a 950,000 kta ethylene plant combined with a 550,00 kta ethylbenzene plant are estimated to be about $560,000 per annum at current energy price levels.

EXAMPLE 2

In a system such as that illustrated in FIG. 2, the effluent 24 is sent to condenser 25 where it is partially condensed. The liquid equivalent to the amount of ethylene required for ethylbenzene production is sent to the ethylbenzene plant 26 via line 24a. The chilled but uncondensed portion of the effluent 24 is sent to the ethylene fractionator as a vapor via line. 24b. In this case the feed to the ethylene fractionator is both reduced as well as enriched. Energy is saved in the ethylene fractionator but is partly lost in the form of lower recuperation from ethane recycle and in the form of higher reflux requirements in the deethanizer 21 to reduce the propylene content of the deethanizer overhead (dilute ethylene). The purity of the ethylene feed 24a to the ethylbenzene plant 16 in this case is about 72 mol % to about 78 mol %. The purity level is expected to cause reduced steam production in the ethylbenzene plant. However, without considering the impact in the ethylbenzene plant the savings in operating costs for a 950,000 kta ethylene-plant combined with a 550,000 kta ethylbenzene plant are estimated to be about $580,000 per annum at current energy price levels.

EXAMPLE 3

In a system such as that illustrated in FIG. 3, the entire effluent 34 from the acetylene converter 33 is sent to the ethylene fractionator 37 and the dilute ethylene feed to the ethylbenzene plant 36 is drawn off via stream 35 as a vapor from the stripping portion of the ethylene fractionator 37. Energy is saved in the ethylene fractionator 37 but is partly lost in the form of lower recuperation from ethane recycle and in the form of a higher reflux requirements in the deethanizer 31 to reduce the propylene content of the deethanizer overhead (dilute ethylene). The purity of the dilute ethylene stream 35 is about 60 mol % to about 65 mol %. The purity level is expected to cause reduced steam production in the ethylbenzene plant. However, without considering the impact in the ethylbenzene plant the savings in operating cost for a 950,000 kta ethylene plant combined with a 550,000 kta ethylbenzene plant are estimated to be about $850,000 per annum at current energy price levels.

EXAMPLE 4

In system such as that illustrated in FIG. 4, the entire effluent 44 from the acetylene converter 43 is sent to the ethylene fractionator 47 and the dilute ethylene feed to the ethylbenzene plant 46 is drawn off via stream 45 as a liquid from the rectification portion of the ethylene fractionator 47. Energy is saved in the ethylene fractionator 47 but is partly lost in the form of lower recuperation from ethane recycle. A higher reflux requirement in the deethanizer is not needed for this case since the side-draw is taken above the feed where propylene concentration is already sufficiently low. The purity of the dilute ethylene stream 45 is about 82 mole % to about 85 mol %. This case produces the highest purity of dilute ethylene feed and has no significant impact in the ethylbenzene plant. The savings in operating cost for a 950,000 kta ethylene plant combined with a 550,000 kta ethylbenzene plant are estimated to be about $780.000 per annum at current energy price levels.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for the production of ethylbenzene comprising the steps of:
   a) cracking a hydrocarbon to provide an olefin-containing effluent;
   b) separating out a $C_2$ component stream from the olefin-containing effluent;
   c) removing acetylene from the $C_2$ component stream to provide a dilute ethylene stream containing ethylene and ethane;
   d) separating the dilute ethylene stream into a first portion to be sent to an alkylator and a second portion to be fed to an ethylene fractionator to separate the ethylene and ethane components of the second portion;
   e) condensing the alkylator feed to provide an alkylator feed stream; and
   f) directing the alkylator feed stream to the alkylator for reaction with benzene to provide an ethylbenzene product.

2. The process of claim 1 wherein the separating step (b) is performed by distillation.

3. A process for the production of ethylbenzene comprising the steps of:
   a) cracking a hydrocarbon to provide an olefin-containing effluent;
   b) separating out a $C_2$ component stream from the olefin-containing effluent;
   c) removing acetylene from the $C_2$ component stream to provide a first dilute ethylene stream containing ethylene and ethane;
   d) feeding the dilute ethylene stream to an ethylene fractionator to separate the ethylene and ethane components of the second portion;
   e) drawing off a side stream from the ethylene fractionator to provide an alkylator feed stream; and
   f) directing the alkylator feed stream to the alkylator for reaction with benzene to provide an ethylbenzene product.

4. The process of claim 3 wherein the side stream is withdrawn at a point below the feed point to provide an alkylator feed having an ethylene content less than that of the dilute ethylene stream fed to the ethylene fractionator.

5. The process of claim 3 wherein the side stream is withdrawn at a point above the feed point to provide an alkylator feed having an ethylene content higher than that of the dilute ethylene stream fed to the ethylene fractionator.

\* \* \* \* \*